United States Patent [19]

Cagnon et al.

[11] Patent Number: 4,592,872
[45] Date of Patent: * Jun. 3, 1986

[54] PROCESS FOR THE SYNTHESIS OF α-CHLORINATED CHLOROFORMATES

[75] Inventors: Guy C. Cagnon, Ballancourt; Marc D. Piteau, Itteville; Jean-Pierre G. Senet, La Chapelle, all of France; Roy A. Olofson; Jonathan T. Martz, both of State College, Pa.

[73] Assignee: Societe Nationale des Poudres et Explosifs, Paris, France

[*] Notice: The portion of the term of this patent subsequent to Jun. 3, 2003 has been disclaimed.

[21] Appl. No.: 341,893

[22] Filed: Jan. 22, 1982

Related U.S. Application Data

[62] Division of Ser. No. 260,907, May 6, 1981.

[30] Foreign Application Priority Data

May 14, 1980 [FR] France ............................... 80 10806

[51] Int. Cl.$^4$ ..................... C07C 68/02; C07C 69/96
[52] U.S. Cl. .................................. 558/281; 558/282; 558/283
[58] Field of Search .......................................... 260/463

[56] References Cited

U.S. PATENT DOCUMENTS 2,820,810  1/1958  Frevel et al. .................. 260/463

FOREIGN PATENT DOCUMENTS

| | | |
|---|---|---|
| 34536 | 8/1981 | European Pat. Off. . |
| 0040153 | 11/1981 | European Pat. Off . |
| 57422 | 8/1982 | European Pat. Off. . |
| 61162 | 9/1982 | European Pat. Off. . |
| 82404 | 6/1983 | European Pat. Off. . |
| 121223 | 6/1900 | Fed. Rep. of Germany . |
| 2628410 | 1/1978 | Fed. Rep. of Germany . |
| 2201870 | 5/1974 | France . |
| 2387988 | 11/1978 | France . |
| 2482587 | 11/1981 | France . |
| 1598568 | 8/1981 | United Kingdom . |

OTHER PUBLICATIONS

Macko, et al., Chemical Abstracts, vol. 53, 22706f (1959).
Czechoslovakian Article, "Aliphatic Esters of Carbamic Acid" by Macko and Gaher, Chem. Zvesti 13, pp. 436–445 (1959).
Müller Liebig's Annalen der Chimie, (1890), vol. 257, p. 50–66.
Beilstein, 4th Ed. vol. 3, pp. 12–13 (1921).
Childs et al., J. Chem. Soc., p. 2180–2183 (1948).
Matzner et al., "The Chemistry of Chloroformates", Chem. Review, 64, pp. (646–650 and 677–687), 1964.
Hennig, Chemical Abstracts, vol. 31, 23116 (1937).
Brysova, et al., Chemical Abstracts, vol. 84, 105502c (1976).
Olofson, et al., Chemical Abstracts, vol. 86, 71966f (1977).
Sugano, et al., Chemical Abstracts, vol. 90, 137829e, 137830y (1979).
Choi, Chemical Abstracts, vol. 92, 198390t (1980).
Mogyorodi, et al., Chemical Abstracts, vol. 95, 24530k (1981).

*Primary Examiner*—Donald G. Daus
*Assistant Examiner*—Diana G. Rivers
*Attorney, Agent, or Firm*—Bucknam and Archer

[57] ABSTRACT

Process for the synthesis of α-chlorinated chloroformates, and new α-chlorinated chloroformates.

The invention relates to a new process for the manufacture of α-chlorinated chloroformates and, to new α-chlorinated chloroformates as new industrial products.

The process according to the invention consists of a synthesis, by catalytic phosgenation, of α-chlorinated chloroformates of the formula:

$$R + CH-O-C-Cl)_m,$$
$$\quad\quad\; | \quad\quad\; \|$$
$$\quad\quad\; Cl \quad\; O$$

in which: R represents a substituted or unsubstituted hydrocarbon radical and m represents an integer superior or equal to one, this synthesis consisting in reacting phosgene with the aldehyde R—CHO)$_m$, in the presence of a catalyst which is an organic or inorganic substance which is capable in a medium containing an aldehyde of the formula R—CHO)$_m$, phosgene and, possibly, a solvent, of generating a pair of ions one of which is an halogenide anion and the other is a cation which is sufficiently separated from said halogenide anion so as to give to the latter a nucleophilic power enabling it to react with the function(s) aldehyde of the molecule R—CHO)$_m$.

8 Claims, No Drawings

PROCESS FOR THE SYNTHESIS OF α-CHLORINATED CHLOROFORMATES

This is a division of application Ser. No. 260,907, filed May 6, 1981.

The invention relates to the manufacture of α-chlorinated chloroformates and to new α-chlorinated chloroformates as industrial products.

The synthesis of α-chlorinated chloroformates of the general formula:

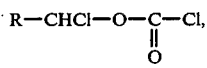

in which R is an aliphatic or aromatic substituent, is a very difficult undertaking if it is essential not to add another chlorine atom to the radical R during the synthesis.

In Liebig's Annalen der Chemie of 1890, Volume 257, page 50 et seq., Müller proposed a process which is still the only one known and used at the present time. This processs consists in chlorinating the corresponding chloroformate which is unsubstituted in the α-position. Unfortunately, numerous by-products which are more highly chlorinated than necessary are obtained in addition to the desired product. Thus, Müller counted no fewer than five by-products in the case of ethyl chloroform which he studied.

Now, the presence of these by-products is extremely troublesome because of the main purpose for which the said chloroformates are applied, namely their conversion to carbonates which are especially useful in the synthesis of fine pharmaceutical products.

It is thus essential to distil the reaction product, although this is difficult because of the presence of numerous by-products.

There is another early publication, namely German Pat. No. 121,223 of 1901, which describes the synthesis of 1,2,2,2-tetrachloroethyl chloroformate and α-chlorobenzyl chloroformate by the phosgenation of chloral and benzaldehyde, respectively, in the presence of a stoichiometric amount of a tertiary amine which does not belong to the pyridine series.

If it is decided to attempt the phosgenation of aldehydes other than those above, for example acetaldehyde, under the same conditions, the formation of numerous byproducts is observed in addition to that of α-chloroethyl chloroformate, which is only obtained with a mediocre yield; this makes the process of no value on the industrial scale.

Furthermore, if it is also decided to attempt the phosgenation with an aliphatic tertiary amine, for example triethylamine, this amine is found to be essentially destroyed, only a very small amount of the derived chloroformate being formed.

There is therefore a great need of a process for the manufacture of pure α-chlorinated chloroformates, if possible with a good yield, which will at last make it possible to guarantee these products, of very simple structure, the development which they deserve.

Applicants have found such a process for the manufacture of α-chlorinated chloroformates free of by-products of subsequent substitution, which process uses inexpensive starting materials and leads to excellent yields.

The invention consists of a process for the synthesis of α-chlorinated chloroformates of the formula:

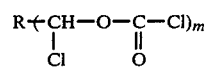

in which R represents a substituted or unsubstituted aliphatic, cyloaliphatic or aromatic hydrocarbon radical and m represents an integer equal to one or 2, characerised in that phosgene is reacted with the corresponding aldehyde, R$-(CHO)_m$, in the presence of a catalyst.

According to the invention, phosgene is reacted with the aldehyde R$-(CHO)_m$ in the presence of a catalyst.

As catalysts according to the invention, the following substances, as such or under the form of their reaction product with phosgene, may notably be cited: tertiary amines, substituted amides, substituted ureas, tertiary phosphines, substituted phosphoramides.

The invention also relates, by way of new industrial products, to the α-chlorinated chloroformate which can be obtained by the process according to the invention and which are particularly useful as agents for synthesis.

The invention is thus remarkable in several respects: it makes it possible to phosgenate a large number of aldehydes and it demonstrates the possibility of carrying out this phosgenation in the presence of catalytic amounts of a very large variety of substances.

The process according to the invention makes it possible to phosgenate a large number of aldehydes with phosgene in the presence of a solvent.

The radical R can thus be a substituted or unsubstituted, saturated or unsaturated aliphatic or cycloaliphatic radical. It is thus possible, according to the invention, to phosgenate aldehydes as different as acetaldehyde, valeraldehyde, chloral, acrolein and cyclohexanecarboxaldehyde.

The radical R can also be a substituted or unsubstituted aromatic radical.

It is thus possible, according to the invention, to phosgenate benzaldehyde, 2-chlorobenzaldehyde and terephthalaldehyde.

As has already been stated above, the process according to the invention consists in phosgenating the aldehyde corresponding to the desired α-chlorinated chloroformate, in the presence or in the absence of a solvent, in the presence of a catalyst present in the reaction medium in the ratio of 1–10% moles and preferably 5–10% moles with respect to the molar quantity of the aldehyde. In the present description, the term "catalyst" is to be taken as having a restricted meaning. The compound added as a catalyst is essential for the reaction to proceed correctly, does not participate directly in the reaction and is used in relatively small amounts compared with the aldehyde; in this sense, it is indeed a catalyst; however, in contrast to that which is commonly known in the case of catalysts, it cannot always be re-used for another reaction once the introduction of phosgene has been stopped, and the applicants do not have any theoretical explanations of this phenomenon to put forward. It has been observed that the most valuable results are obtained with the following catalysts: aromatic tertiary amines containing a single aromatic nucleus, such as pyridine, N,N-dimethylaniline, N,N-dimethylaminopyridine pyridine imidazole, substituted amides and more particularly dimethylformamide, substituted ureas and thioureas and more particularly tetralkyl(thio)ureas, such as tetrabutylurea, tertiary phosphines and especially aliphatic tertiary phosphines, such as trioctylphosphine, and substituted phosphoramides and more particularly hexamethylphosphotriamide.

With the catalysts of the group comprising amides, ureas and tertiary phosphines, or with pyridine, phosgenation carried out at between 0° and 70° C. already gives good results; this is the case especially with catalysts like carboxamides, such as dimethylformamide, phosphoramides, such as hexamethylphosphotriamide, tetraalkyl-ureas or -thioureas, such as tetrabutylurea, tertiary phosphines, such as trioctyl phosphine, and of course pyridine. These catalysts will preferably be chosen if it is desired, for certain reasons, in particular the instability of the α-chlorinated chloroformate, to carry out the phosgenation at a moderate temperature.

With tertiary amines containing a single aromatic nucleus, such as N,N-dimethylaminopyridine or N,N-dimethylaniline, or also with imidazole, the phosgenation is preferably carried out above 70° C.

According to the invention, the phosgenation is generally carried out under atmospheric pressure, but, in certain cases, it can be advantageous to carry out the reaction under a pressure which is above or below normal pressure; for example, in the case of the phosgenation of a volatile aldehyde, it can be useful to carry out the reaction under a pressure which is slightly above normal pressure.

The reaction may be carried out in a solvent. This solvent is advantageously chosen, from amongst nonpolar or weakly polar and aprotic solvents, such as, for example, carbon tetrachloride, chloroform, methylene chloride, toluene, chlorobenzene and hexane.

Nevertheless, insofar as it is desired to phosgenate a very reactive aldehyde, such as, for example, acetaldehyde, a solvent which is slightly more polar than carbon tetrachloride is preferably chosen so as to avoid the risk of the formation of dichlorinated carbonate, and methylene chloride, for example, is thus preferred; in this case, it can also be advantageous to carry out the phosgenation at a relatively low temperature (35°-40° C.).

The actual phosgenation reaction is carried out in accordance with the conventional techniques known to those skilled in the art. Thus, it is possible either to mix a solution of the phosgene in part of the solvent with a solution of aldehyde containing the catalyst, or also to bubble phosgene gas into a solution of aldehyde containing the catalyst. The actual phosgenation lasts several hours and is generally carried out in a stirred medium. After phosgenation, the α-chlorinated chloroformate is generally isolated from the reaction medium by conventional distillation.

Applicants have observed in this respect that, in the case of the synthesis of α-chlorinated chloroformates of the benzyl series, it is preferred to use pyridine as the catalyst with carbon tetrachloride as the solvent because, under these conditions, the catalyst or its reaction-product with phosgene precipitates after phosgenation, and this makes it possible to isolate the α-chlorinated chloroformate by simple filtration, without distillation.

α-Chlorinated chloroformates are in great demand as agents for synthesis, in particular for the synthesis of fine pharmaceutical products. The invention also relates, by way of industrial products, to the new α-chlorinated chloroformates of the formula

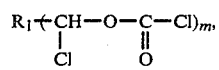

in which m represents an integer of one or two and $R_1$ represents: a substituted or unsubstituted saturated aliphatic radical containing at least two carbon atoms, a substituted or unsubstituted, unsaturated aliphatic radical, a substituted or unsubstituted cycloaliphatic radical or a substituted aromatic radical.

The invention relates more particularly to the α-chlorinated chloroformates obtained from the following aldehydes: valeraldehyde, acrolein, 2-chlorobenzaldehyde, terephthalaldehyde and cyclohexanecarboxaldehyde.

It is in fact one of the advantages of the present invention that it makes it possible to obtain new α-chlorinated chloroformates which have not been described hitherto in the literature and which, in certain cases, cannot be obtained by the processes known hitherto, such as, in particular, the α-chlorinated chloroformates obtained from unsaturated aldehydes.

The examples given below illustrate the invention without limiting its scope.

EXAMPLE 1

44 g (1 mol) of freshly distilled acetaldehyde, 200 ml of anhydrous carbon tetrachloride and 120 g (1.2 mols) of phosgene are placed in a 500 ml reactor equipped with a stirrer, a thermometer, a solid carbon dioxide condenser and a dropping funnel. With the mixture kept at 0° C., 28.4 g (0.1 mol) of tetra-n-butylurea are added in the course of 15 minutes. The temperature is raised to 40° C. and the reaction is continued for 2 hours 30 minutes. After removal of the excess phosgene by degassing and of the solvent by evaporation, 72 g of 1-chloroethyl chloroformate, which distils at 117° C. (the literature indicates 115°-116° C.), are obtained, which corresponds to a yield of 50% by weight. As the formula of the product is:

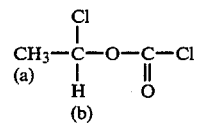

the infra-red spectrum shows a band at 1,780 cm$^{-1}$, corresponding to the C=O double bond, whilst the NMR spectrum, run in deuterated chloroform with tetramethylsilane as the reference, shows a doublet at 1.85 ppm, corresponding to the protons (a), and a quadruplet at 6.44 ppm, corresponding to the proton (b).

EXAMPLE 2

This example relates to the synthesis of α-chloroethyl chloroformate from acetaldehyde, in the presence of hexamethylphosphotriamide. 1,000 ml of methylene chloride, washed with water and dried over magnesium sulphate, 440 g (10 mols) of anhydrous crude acetaldehyde and 179 g (1 mol) of hexamethylphosphorotriamide are introduced into a 3 liter glass reactor fitted with an anchor stirrer, a thermometer, a −35° C. condenser and a dip tube. The mixture is cooled to −5° C. and 1,107 g of phosgene gas are introduced in the course of 6 hours 30 minutes, whilst stirring.

The temperature of the reaction medium is then raised to 35°–40° C. and this temperature is maintained for 3 hours.

The mixture is left to stand overnight at ambient temperature and the excess phosgene is then removed by sweeping with nitrogen for 2 hours 30 minutes.

The mixture obtained is then distilled under 150 mm Hg in a glass column (height: 40 cm, diameter: 3 cm, packed with 0.5 cm Fenske helices) and the fraction passing over at 68° C. is collected.

1,020.4 g of α-chloroethyl chloroformate are thus obtained, which corresponds to a yield of 71%, relative to the acetaldehyde used.

Analysis: infra-red spectrum (C=O): 1,780 cm$^{-1}$; $n_D^{20}$: 1.4220; density $d_{15}^{15}$: 1.2946.

EXAMPLE 3

This example relates to the synthesis of α-chloroethyl chloroformate from acetaldehyde, in the presence of pyridine.

100 ml of methylene chloride, washed with water and dried over magnesium sulphate, 44 g (1 mol) of anhydrous crude acetaldehyde and 7.9 g (0.1 mol) of freshly distilled pyridine are introduced into a 500 ml glass reactor equipped with an anchor stirrer, a thermometer and an acetone/solid carbon dioxide reflux condenser. The mixture is cooled to between −5° and −10° C. and 120 g of phosgene are added in the course of about 1 hour.

The mixture is then heated under gentle reflux (temperature between 40° and 45° C.) for 3 hours 30 minutes.

The insoluble materials are filtered off under nitrogen and the filtrate is distilled under reduced pressure. 90 g (yield: 63%) of α-chloroethyl chloroformate (boiling point: 68° C./150 mm Hg) are thus obtained.

EXAMPLE 4

This example relates to the synthesis of the α-chlorinated chloroformate obtained from valeraldehyde.

21.5 g (0.25 mol) of n-pentanal, 50 ml of carbon tetrachloride and 1.9 g (0.025 mol) of pyridine are introduced into a 100 ml reactor equipped as above. 30 g (0.3 mol) of phosgene are added to this mixture, cooled to −5° C., in the course of 30 minutes. The temperature is gradually raised to 40° C. After one hour at this temperature, the reaction mixture is degassed with nitrogen and filtered and the filtrate is distilled under reduced pressure. The α-chloro-n-pentyl chloroformate distils at 73° C. under 15 mm of mercury. Weight obtained: 28 g, which corresponds to a yield of 60.5%.

Infra-red spectrum: C=O: 1,790 cm$^{-1}$; $n_D^{20}$: 1.4377; density (20° C.): 1.1523.

NMR (CDCl₃, TMS):

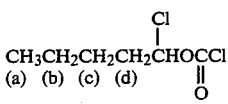

(a) hump at 0.92 ppm (3H)
(b) hump at 1.40 ppm (4H)
(c) hump at 2.05 ppm (2H)
(d) triplet at 6.30 ppm (1H)

EXAMPLE 5

This example relates to the synthesis of the α-chlorinated chloroformate obtained from acrolein.

The equipment and the procedure are identical to those of Example 4 and the following starting materials are used:

acrolein (propenal): 28 g (0.5 mol)
pyridine: 3.95 g (0.05 mol)
carbon tetrachloride: 50 ml
phosgene: 60 g (0.6 mol)

The α-chloroallyl chloroformate distils at 38° C. under 10 mm of mercury.

Weight obtained: 42 g, which corresponds to a yield of 54%.

Infra-red spectrum: C=O: 1,780 cm$^{-1}$; $n_D^{20}$: 1.4462, density (20° C.): 1.2853.

NMR spectrum:

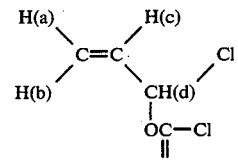

(a)(b)(c): complex hump from 5.2 to 6.5 ppm (3H)
(d): doublet at 6.71 ppm (1H)

EXAMPLE 6

This example relates to the synthesis of the α-chlorinated chloroformate obtained from benzaldehyde.

The products used are as follows:

benzaldehyde: 26.5 g (0.25 mol)
pyridine: 1.95 g (0.025 mol)
phosgene: 35 g (0.35 mol)
carbon tetrachloride: 50 ml Using a procedure identical to that of Example 4, 34.8 g (68%) of α-chlorobenzyl chloroformate, which distils at 70° C. under 0.4 mm of mercury, are obtained.

Infra-red spectrum: C=O: 1,770 cm$^{-1}$; $n_D^{20}$: 1.5367; density (20°): 1.3016.

NMR spectrum:

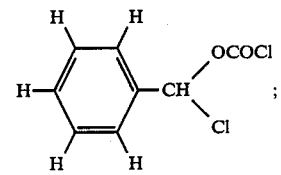

all the protons have a chemical shift of between 7 and 8 ppm.

EXAMPLE 7

This example relates to the synthesis of the α-chlorinated chloroformate obtained from 2-chlorobenzaldehyde.

Compared with Example 6, the benzaldehyde is replaced by 2-chlorobenzaldehyde.

25.1 g (yield: 42%) of α-chloro-2-chlorobenzyl chloroformate, which distils at 85°–88° C. under 0.2 mm Hg, are obtained.

Infra-red spectrum: C=O: 1,780 cm$^{-1}$; $n_D^{20}$: 1.5420; density (20° C.): 1.4294.

NMR spectrum:

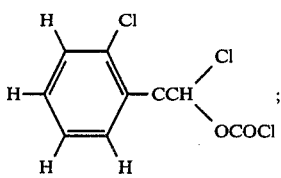

all the protons have a chemical shift of between 7 and 8 ppm.

EXAMPLE 8

This example relates to the synthesis of the α-chlorinated chloroformate obtained from terephthalaldehyde.

67 g (0.5 mol) of terephthalaldehyde, 3.95 g (0.05 mol) of pyridine and 100 ml of carbon tetrachloride are placed in a 500 ml reactor. 120 g (1.2 mols) of phosgene are then introduced at 0° C. The mixture is then heated gradually to 40° C. and kept at this temperature for 3 hours. After degassing, filtration and removal of the solvent, 133 g (yield: 80%) of a colourless oil are obtained.

Total chlorine content: calculated: 42.7, found: 40.02%.

IR spectrum: C=O: 1,780 cm$^{-1}$
NMR spectrum (CDCl$_3$, TMS):

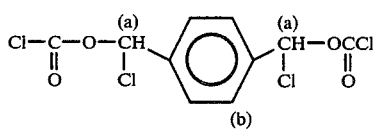

(a) singlet at 7.29 ppm (2H)
(b) singlet at 7.64 ppm (4H)

EXAMPLE 9

This example relates to the synthesis of α-chloroethyl chloroformate from acetaldehyde, in the presence of trioctylphosphine.

11 g (0.25 mol) of acetaldehyde, 9.25 g (0.025 mol) of trioctylphosphine and 50 ml of carbon tetrachloride are placed in a 100 ml reactor. 30 g (0.3 mol) of phosgene are added to this mixture, cooled to 0° C. After heating at 35°–40° C. for 1 hour, the reaction mixture is degassed and distilled under reduced pressure (150 mm Hg). 9.1 g (yield: 25%) of α-chloroethyl chloroformate, which distils at 67°–68° C., are thus obtained.

EXAMPLE 10

This experiment relates to the preparation of α-chloroethyl chloroformate by the phosgenation of acetaldehyde in the presence of 5 mol % of pyridine, in a solvent medium.

The procedure and the equipment are identical to those of Example 4.

The amounts of products used are as follows:
acetaldehyde: 11 g (0.25 mol)
pyridine: 0.99 g (0.0125 mol)
phosgene: 30 g (0.3 mol)
methylene chloride: 50 ml 25.6 g (yield: 71.6%) of α-chloroethyl chloroformate, which distils at 68° C. under 150 mm of mercury, are thus obtained.

EXAMPLE 11

This experiment relates to the preparation of α-chloroethyl chloroformate by the phosgenation of acetaldehyde in the presence of 5 mol % of pyridine, without a solvent.

22 g (0.5 mol) of acetaldehyde and 1.98 g (0.025 mol) of pyridine are placed, at 0° C., in a 100 ml reactor equipped as in the preceding examples. 60 g (0.6 mol) of phosgene are introduced at this temperature. The reaction mixture is heated to 30° C. in the course of four hours and kept at this temperature for 1 hour. After removal of the phosgene, 42.1 g (yield: 59%) of α-chloroethyl chloroformate, which distils at 68° C. under 150 mm of mercury, are obtained.

EXAMPLE 12

This experiment relates to the phosgenation of cyclohexanecarboxaldehyde.

28 g (0.25 mol) of cyclohexanecarboxaldehyde, 1.98 g (0.025 mol) of pyridine and 50 ml of carbon tetrachloride are placed in a 100 ml reactor. With this mixture cooled to 0° C., 30 g (0.3 mol) of phosgene are introduced. The reaction medium is then heated to 35°–40° C. and kept at this temperature for 1 hour.

After degassing, filtration and removal of the solvent under reduced pressure, 46 g (yield: 87%) of the expected chloroformate, which distils at 90°–93° C. under 10 mm of mercury, are obtained.

$n_D^{20}$: 1.4738, density (20° C.): 1.1934.
NMR spectrum (CDCl$_3$, TMS):

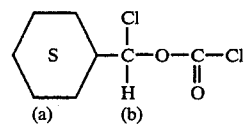

(a) hump from 1.15 to 2.2 ppm (11H)
(b) doublet at 6.1 ppm (1H)

EXAMPLES 13 to 17

The purpose of these examples, which are carried out with the equipment of Example 4, is to illustrate the efficiency of various catalysts as a function of the temperature.

Each of these experiments was carried out on the following amounts:
acetaldehyde: 4.4 g (0.1 mol)
toluene: 45 g
catalyst: 0.01 mol
phosgene: 12 g (0.12 mol)

The results obtained as a function of the temperature after a reaction time of 3 hours are shown in the table below, it being specified that the sign of a reaction or the absence of a reaction is assessed by infra-red spectrophotometry. The absence of a reaction indicates that the yield is below 5%.

| EXAMPLE No. | CATALYST | 40° C. | 70° C. | 100° C. |
|---|---|---|---|---|
| 13 | N,N—dimethylaminopyridine | no reaction | no reaction | reaction |
| 14 | N,N—dimethylaniline | no reaction | reaction | — |
| 15 | imidazole | no reaction | no reaction | reaction |
| 16 | reaction product of tetra n-butylurea with phosgene | reaction | — | — |

| EXAMPLE No. | CATALYST | 40° C. | 70° C. | 100° C. |
|---|---|---|---|---|
| | 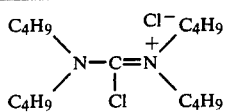 | | | |
| 17 | dimethylformamide | | reaction | |

We claim:

1. The process for the synthesis of α-chlorinated chloroformates of the formula:

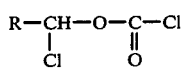

wherein: R is alkyl of 1 to 4 carbon atoms, or R is—$CCl_3$ which consists of reacting phosgene with an aldehyde of formula RCHO, wherein R has the same meaning as above in the presence of 1–10% mole of a catalyst which is a member selected from the group consisting of pyridine, N,N-dimethylaminopyridine, imidazole, tertiary aliphatic phosphines, and a member of the group of amides, ureas, thioureas, phosphoramides wherein the N atoms are completely substituted by alkyl groups and the products of reactions of these catalysts with phosgene.

2. Process according to claim 1 wherein the catalyst is a member selected from the group consisting of pyridine, N,N-dimethylaminopyridine, dimethylforamide, tetra-n-butyl urea, trioctyl phosphine, hexamethyl phosphotriamide and imidazole.

3. The process according to claim 1 wherein the reaction is carried out in a solvent which is carbon tetrachloride, chloroform, dichloromethane, toluene, chlorobenzene or hexane.

4. The process according to claim 2 wherein the catalyst is dimethylformamide, hexamethylphosphotriamide, tetra-n-butyl urea, trioctylphosphine or pyridine and the temperature is 0°–70° C.

5. The process according to claim 2 wherein the catalyst is N,N-dimethylamino pyridine, imidazole, and the temperature is in excess of 70°.

6. The process according to claim 1 wherein the aldehyde is acetaldehyde, the catalyst is tetra n-butyl urea, the reaction is carried out in dichloromethane or carbon tetrachloride and the temperature does not exceed 40° C. during the reaction with phosgene.

7. The process according to claim 1 wherein the amount of the catalyst is 5% mole with respect to the molar amount of said aldehyde.

8. The process according to claim 1 wherein the aldehyde is acetaldehyde, valeraldehyde or chloral.

* * * * *

UNITED STATES PATENT AND TRADEMARK OFFICE
CERTIFICATE OF CORRECTION

PATENT NO. : 4,592,872
DATED : June 3, 1986
INVENTOR(S) : Guy Cagnon et al

It is certified that error appears in the above-identified patent and that said Letters Patent is hereby corrected as shown below:

On the title page inventors should read

-- (75) Inventors: Guy C. Cagnon, Ballancourt; Marc D. Piteau, Itteville; Jean-Pierre G. Senet, La Chapelle, all of France --.

Signed and Sealed this

Sixteenth Day of September 1986

[SEAL]

Attest:

Attesting Officer

DONALD J. QUIGG

Commissioner of Patents and Trademarks